United States Patent
Chalas et al.

(10) Patent No.: US 10,878,947 B2
(45) Date of Patent: Dec. 29, 2020

(54) TRIGGERED SENSOR DATA CAPTURE IN A MOBILE DEVICE ENVIRONMENT

(71) Applicant: INTERNATIONAL BUSINESS MACHINES CORPORATION, Armonk, NY (US)

(72) Inventors: Kathleen Chalas, Wappingers Falls, NY (US); Jonathan R. Fry, Fishkill, NY (US); Michael Gschwind, Chappaqua, NY (US); John S. Houston, Hopewell Junction, NY (US); Alexander C. Leventhal, Wappingers Falls, NY (US); Cameron E. Tidd, Goshen, NY (US); Lahiruka S. Winter, Fishkill, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 734 days.

(21) Appl. No.: 15/355,262

(22) Filed: Nov. 18, 2016

(65) Prior Publication Data
US 2018/0144100 A1    May 24, 2018

(51) Int. Cl.
*G16H 50/20* (2018.01)
*G16H 40/67* (2018.01)
(Continued)

(52) U.S. Cl.
CPC ......... *G16H 10/60* (2018.01); *G08B 21/0453* (2013.01); *G08B 25/08* (2013.01);
(Continued)

(58) Field of Classification Search
CPC ..... A61B 5/02055; A61B 5/0205; A61B 5/00; A61B 5/145; A61B 5/02; A61B 5/024;
(Continued)

(56) References Cited

U.S. PATENT DOCUMENTS 6,055,506 A * 4/2000 Frasca, Jr. ........... G06F 19/3418
705/3
7,970,620 B2    6/2011 Brown
(Continued)

FOREIGN PATENT DOCUMENTS

WO    WO-2005087091 A2 * 9/2005 ........... A61B 5/0002
WO    2013140163 A1    9/2013

OTHER PUBLICATIONS

Mell, Peter, et al., "The NIST Definition of Cloud Computing", NIST Special Publication 800-145, Sep. 2011, Gaithersburg, MD, 7 pgs.

*Primary Examiner* — Fonya M Long
*Assistant Examiner* — Alaaeldin M Elshaer
(74) *Attorney, Agent, or Firm* — Edward Wixted; Matthew M. Hulihan; Heslin Rothenberg Farley & Mesiti PC

(57) ABSTRACT

Triggered sensor data capture in a mobile device environment. A method monitors primary sensor data obtained from first wearable sensor device(s) to determine whether trigger condition(s) are met for triggering supplemental sensor data capture. Based on recognizing a health event, the method obtains health status input from a user, configures second wearable sensor device(s) to obtain supplemental sensor data that includes additional data in addition to the primary sensor data, and obtains the supplemental sensor data. The method provides the health status input and the obtained supplemental sensor data as correlated health event data of the health event for analysis. Based on the analysis, the method tunes at least one trigger condition of the trigger condition(s) to adjust a scope of supplemental sensor data capture.

19 Claims, 7 Drawing Sheets

(51) Int. Cl.
  G08B 25/10 (2006.01)
  G08B 25/08 (2006.01)
  G16H 10/60 (2018.01)
  G08B 21/04 (2006.01)
  G16H 40/63 (2018.01)

(52) U.S. Cl.
  CPC ............. G08B 25/10 (2013.01); G16H 40/63 (2018.01); G16H 40/67 (2018.01)

(58) Field of Classification Search
  CPC ...... A61B 5/6898; G08B 25/10; G08B 25/08; G08B 21/0453; G08B 23/00; G08B 1/08; G16H 10/60; G16H 40/67; G16H 40/63; G06F 19/3481; G06F 17/30; A63B 24/00
  USPC .................................. 705/2, 91, 3; 600/301
  See application file for complete search history.

(56) References Cited

U.S. PATENT DOCUMENTS

| | | | |
|---|---|---|---|
| 8,412,655 B2* | 4/2013 | Colman | A61B 5/0836 |
| | | | 706/16 |
| 8,684,922 B2 | 4/2014 | Tran | |
| 8,751,253 B2 | 6/2014 | Breslau | |
| 8,795,138 B1 | 8/2014 | Yeh et al. | |
| 8,944,958 B1 | 2/2015 | Brumback et al. | |
| 8,945,017 B2* | 2/2015 | Venkatraman | A61B 5/721 |
| | | | 600/500 |
| 9,089,733 B2 | 7/2015 | Fisbein et al. | |
| 9,269,119 B2* | 2/2016 | Warner | G06Q 50/22 |
| 2003/0069753 A1* | 4/2003 | Brown | A61B 5/1171 |
| | | | 705/2 |
| 2008/0146892 A1* | 6/2008 | LeBoeuf | G16H 50/30 |
| | | | 600/300 |
| 2009/0069642 A1* | 3/2009 | Gao | A61B 5/02055 |
| | | | 600/300 |
| 2009/0322513 A1* | 12/2009 | Hwang | A61B 5/02055 |
| | | | 340/539.12 |
| 2011/0112852 A1* | 5/2011 | Ware | G06Q 50/24 |
| | | | 705/2 |
| 2011/0245632 A1* | 10/2011 | Chutani | A61B 8/4411 |
| | | | 600/301 |
| 2011/0251495 A1 | 10/2011 | Province et al. | |
| 2012/0136217 A1* | 5/2012 | Cheung Hyen | A61B 5/02055 |
| | | | 600/300 |
| 2012/0173269 A1 | 7/2012 | Omidi | |
| 2012/0197090 A1 | 8/2012 | Chen | |
| 2013/0116578 A1* | 5/2013 | An | A61B 5/0205 |
| | | | 600/484 |
| 2013/0278414 A1 | 10/2013 | Sprigg et al. | |
| 2014/0088985 A1* | 3/2014 | Grant | G06F 19/325 |
| | | | 705/2 |
| 2014/0222174 A1* | 8/2014 | Teller | A61B 5/01 |
| | | | 700/91 |
| 2014/0243612 A1* | 8/2014 | Li | A61B 5/0205 |
| | | | 600/301 |
| 2014/0257058 A1* | 9/2014 | Clarysse | G06Q 50/22 |
| | | | 600/301 |
| 2015/0112722 A1* | 4/2015 | Dees | A61B 5/7275 |
| | | | 705/3 |
| 2016/0170998 A1* | 6/2016 | Frank | G06F 16/24578 |
| | | | 707/748 |
| 2016/0188839 A1* | 6/2016 | Kaul | G06F 19/00 |
| | | | 705/2 |
| 2017/0258338 A1* | 9/2017 | Presura | A61B 5/02416 |

* cited by examiner

TRIGGERED SENSOR DATA CAPTURE IN A MOBILE DEVICE ENVIRONMENT

BACKGROUND

With the advent of wearable technology comes greater ability to collect data of interest, for instance health or medical-related data of an individual. This data may be useful in diagnosing and treating health conditions. Doctors typically ask patients about the circumstances surrounding a health event, such as what was happening at the time of the event and any specific symptoms that the individual experienced. This feedback may be subjective, without relevance to the cause of the event, incomplete and/or of little value without supporting data. Even if the individual is monitored by, for instance, a wearable device, often times data captured around the time of the event is lost by the time the individual can get to proper medical assistance. Even when some data has been logged, there may be an issue combining the data with information about what the patient was experiencing or doing at the time of the event to inform an intelligent diagnosis and therefore treatment of a potential problematic health condition.

SUMMARY

Shortcomings of the prior art are overcome and additional advantages are provided through the provision of a computer-implemented method. The method monitors primary sensor data obtained from first wearable sensor device(s) to determine whether trigger condition(s) are met for triggering supplemental sensor data capture. Based on recognizing a health event, the method obtains health status input from a user, configures second wearable sensor device(s) to obtain supplemental sensor data that includes additional data in addition to the primary sensor data, and obtains the supplemental sensor data. The method provides the health status input and the obtained supplemental sensor data as correlated health event data of the health event for analysis. Based on the analysis, the method tunes at least one trigger condition of the trigger condition(s) to adjust a scope of supplemental sensor data capture.

Further, a computer program product including a computer readable storage medium readable by a processor and storing instructions for execution by the processor is provided for performing a method. The method monitors primary sensor data obtained from first wearable sensor device(s) to determine whether trigger condition(s) are met for triggering supplemental sensor data capture. Based on recognizing a health event, the method obtains health status input from a user, configures second wearable sensor device(s) to obtain supplemental sensor data that includes additional data in addition to the primary sensor data, and obtains the supplemental sensor data. The method provides the health status input and the obtained supplemental sensor data as correlated health event data of the health event for analysis. Based on the analysis, the method tunes at least one trigger condition of the trigger condition(s) to adjust a scope of supplemental sensor data capture.

Yet further, a computer system is provided that includes a memory and a processing unit in communication with the memory, wherein the computer system is configured to perform a method. The method monitors primary sensor data obtained from first wearable sensor device(s) to determine whether trigger condition(s) are met for triggering supplemental sensor data capture. Based on recognizing a health event, the method obtains health status input from a user, configures second wearable sensor device(s) to obtain supplemental sensor data that includes additional data in addition to the primary sensor data, and obtains the supplemental sensor data. The method provides the health status input and the obtained supplemental sensor data as correlated health event data of the health event for analysis. Based on the analysis, the method tunes at least one trigger condition of the trigger condition(s) to adjust a scope of supplemental sensor data capture.

Additional features and advantages are realized through the concepts described herein.

BRIEF DESCRIPTION OF THE DRAWINGS

Aspects described herein are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Described herein are facilities for triggered sensor data capture, for instance to assist in the capture of health information. Aspects include monitoring, via primary sensor data, biometric and other parameters, recognizing health events, and triggering supplemental sensor data capture. User-provided self-perceived heath status is correlated to the supplemental sensor data for analysis to provide valuable health-related information about the individual and continued targeted sensor data monitoring.

Figure 1:
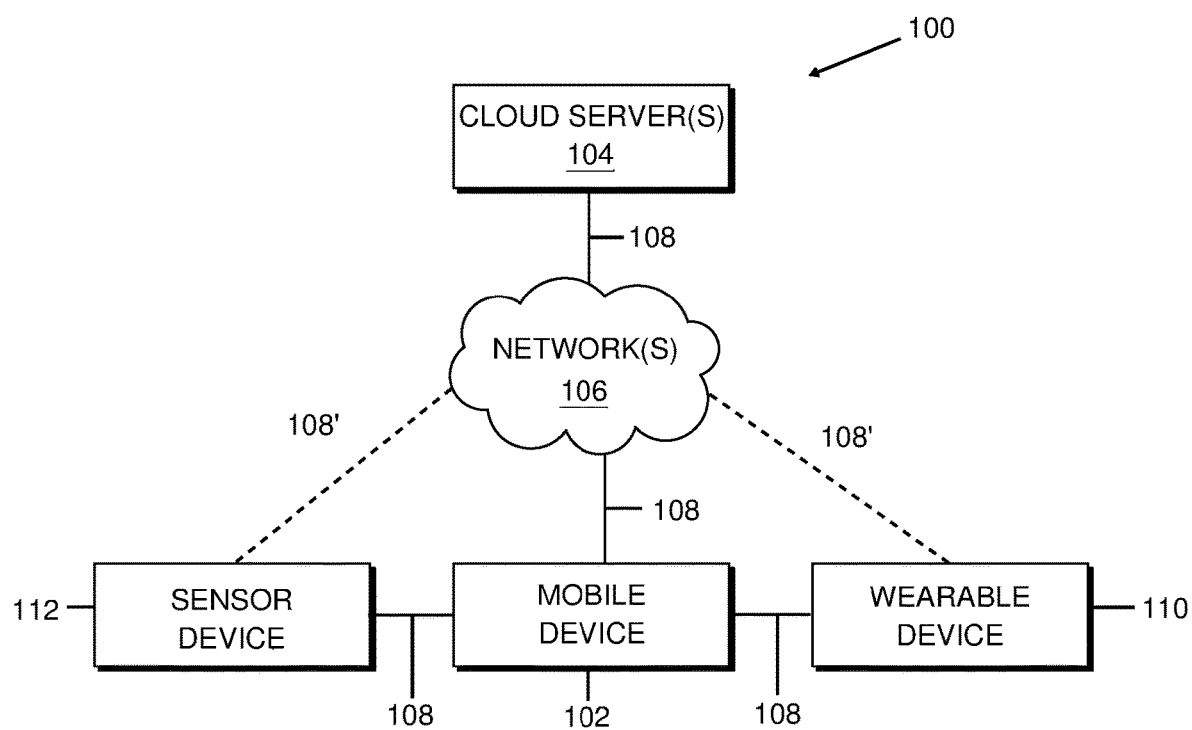
FIG. 1 depicts an example environment to incorporate and use aspects described herein.

FIG. 1 depicts an example environment 100 to incorporate and use aspects described herein. Environment 100 includes mobile device 102 that communicates with cloud server(s) 104 via network(s) 106. Network(s) 106 include one or more wired and/or wireless networks, such as one or more local area networks and/or one or more wide area networks, such as the internet. Cloud server(s) 104 include one or more remote computer systems/servers providing cloud-hosted facilities.

Mobile device 102 communicates in this example with remote devices, including wearable device 110, sensor device 112, and cloud server(s) 104, across wired and/or wireless communication paths 108. In some examples, mobile device 102 communicates with a remote device such as a wearable device through a direct communication path by pairing with the remote device. An example direct communication path is a Bluetooth® or Wi-Fi Direct connection between the two devices. Wearable device 110 and/or sensor device 112 may communicate with network(s) 106 through mobile device 102. Optionally, as shown in FIG. 1, wearable device 110 and/or sensor device 112 may communicate directly with network(s) 106 and devices communicating therewith via communications paths 108'.

Mobile device 102 may be any mobile computer system, examples of which include smartphones, tablets, and other types of computer systems. Wearable device 110 may also be implemented as a computer system. Wearable devices (sometimes referred to as 'wearable mobile devices' or just 'wearables') are a type of mobile device. Some wearable devices are provided as wearable eyewear, wrist watches, wristbands, and clip-on devices, as examples. Some wearables are wearable sensor devices that sense and provide biometric data by leveraging sensor(s) included as part of the wearable device or in communication with the wearable device. Fitness/sports trackers and heart rate monitors are just some examples of wearable sensor devices.

Sensor device 112 may also be a data processing system of relatively limited but dedicated capability, configured for a specific task of sensing one or more parameters (such as heart rate, body temperature, etc.) and providing the values to a remote device, such as a wearable device (e.g. 110) or other mobile device (e.g. 102).

FIG. 1 is just one example of an environment to incorporate and use aspects described herein. In other example embodiments, mobile device 102 is or incorporates a wearable device, which itself is or incorporates sensors/sensing devices. In yet other embodiments, the environment incorporates multiple sensor devices, wearable devices and/or mobile devices. As used herein, wearable, wearable device, and wearable sensor device refer to a mobile device including and/or communicating with sensor(s).

Provided herein are facilities for assisting in the capture of health information based upon sets of biometric parameters such as trigger conditions to trigger sensor data capture and user self-perceived health status input. As described above, doctors or other medical personnel may ask a patient for information related to a health event at the time of the event. Such information might include the specific symptoms that the patient experienced. This information may be subjective and/or carry little or no relevance to the cause of the event. With the advent of wearable technology including wearable sensor devices, there is a greater ability to collect data of interest. However, difficulties arise in the combination or correlation of acquired sensor data with information about what the patient was experiencing or doing at the time of the event. Often times data about the event or data acquired when the event occurred is lost by the time the individual reaches medical assistance.

An example challenge is capturing data about the user's self-perceived health status, sometimes referred to herein as 'qualia'. It may be difficult for a device to 'measure' tiredness, mood, and severity of ache or pain, as examples (all of which are examples of a user's self-perceived health status). Journaling or logging at fixed intervals may provide data that is too sparse for many of the potential linkages that may be drawn between acquired sensor data and user qualia. Instead, data-driven triggers to prompt an individual for qualia may provide a better understanding about the causes of health events and further utility for proper medical treatment and user self-improvement.

Recently it has become common to gather data about individuals, hoping to use this data in the future to produce or provide a better product or service. In some applications having the proper facilities, that data may be leveraged and applied instantly to a particular problem. Wearables often gather data and display it to the user. There is potential for technology beyond this use—to be a partner to solutions, rather than just a metric. Wearables can be leveraged to trigger events based on primary or initial data gathering. An example triggered event may be to communicate with the user, such as to provide medical assistance in an emergency. This may be especially useful because a device may be able to better observe a pattern or trend that a user is unlikely to notice or otherwise know about.

By way of specific example, assume that a user consumes cereal once a week and a few hours later experiences headaches. If a device (e.g. mobile, wearable or a combination) had gathered some baseline information, it could ask the user on a cereal day if the user experiences/experienced headache. If the answer is yes, the device may be able to determine that the user's cereal consumption has been correlating with headache frequency. This is a pattern the user may not otherwise notice, especially in cases where the user's cereal consumption is sporadic or there are long periods of time between cereal consumption.

Another example involves a cause and effect relationship. Some health events go hand-in-hand. For instance, a low body temperature causes fatigue. This is typically observed in the evenings—the user's body temperature drops as the time approaches for the user to fall asleep. If the user's body temperature is low during the day but the user perceives only the effect (fatigue), the user may address only this effect, rather than the cause (low body temperature). For instance, the user may consume a food or beverage to address the fatigue rather than move to a warmer environment. A wearable or other device could observe a low body temperature and ask the user whether the user feels tired. If the answer is yes, the device could provide a suggestion that addresses the cause (suggest a solution to raise the user's temperature).

Aspects described herein provide devices and other facilities for gathering a wide array of biometric and/or other data on an ongoing basis, and, when certain parameters are detected, prompting a user for input and logging biometric data and user input as being related to a health event. Initially, primary data obtained from sensor(s) may be monitored for various trigger conditions that may signify a potentially important health-related event. When triggered, additional/supplemental biometric and/or other data can be logged, based on detecting the potentially important health-related event.

Aspects go beyond a mere data collection methodology, extending to approaches for determining when it is most important to collect data and how to align that data with non-sensor qualia data input by the user. Bandwidth of low-power systems may be extremely limiting due to the power and other resources necessary for sensing and logging data. Aspects described herein may differ from approaches that focus on the management of metric-sensor data and compression/sampling techniques. User qualia (self-perceived health status) cannot be automatically gathered by sensors. A typical "sensor" approach to user feedback may not be possible; sampling rate may become prohibitively intrusive when too frequent, and useless when too coarse. Facilities are provided to obtain and align this user feedback/qualia with metric sensor feeds, and use both data streams to create adaptive trigger-capture paradigms for rich contextual data. This tightly coupled contextual data can provide immense value for self-improvement and medical treatment.

Reference herein to sensors/sensor devices can refer to any appropriate, currently available or yet-to-be discovered device for sensing any of various parameters. Example sensors include commercial, off-the-shelf (COTS) integrated sensor packages that may create a data feed. Example such COTS products include those for sensing and/or monitoring heart rate, blood pressure, or skin resistance, camera systems, and two-dimensional (2D)/three-dimensional (3D) accelerometer systems, and/or sensors that communicate using the ANT+ protocol (organized by Dynastream Innovations Inc., Alberta, Canada), as examples, though it is understood that aspects described herein may leverage and use devices for acquiring and providing any appropriate, desired data.

In accordance with aspects described herein, upon detecting a predefined or configurable set of parameters (referred to herein as a trigger condition), a device such as a user's mobile device, smartphone, tablet, or wearable device with a user interface can prompt the user for input. The parameters of a trigger condition can relate to primary sensor data being monitored. There are many potential types of sensors, and therefore sensor data, from which to key-off the parameter detection. In some embodiments, a doctor designs a particular set of parameters for health events or conditions that the doctor would like to focus on for the patient from a diagnosis and/or treatment perspective. A set of parameters may specify 'concurrently elevated heartrate and body temperature', for instance. Some parameters may be based on biometric data or other information controlled or dependent on the user, while other parameters may not. For instance, current time, location, or weather may be parameters used in recognizing a health event and meeting a trigger condition for supplemental data gathering.

A parameter value may be statically set in a trigger event specification. For instance, a parameter may specify 'heartrate <=170'. A detected heartrate at or above 170 would satisfy that parameter, which may or may not meet the associated trigger condition depending on whether there are additional parameters that factor into the trigger condition.

In some examples, a parameter is or includes a dynamic threshold that may be set or ascertained dynamically, and automatically in some examples. For instance, a dynamic threshold may be set dynamically based on statistical analysis of sensor data value(s). An example may be a determined statistical outlier that suggests an abnormal condition. For instance, if a user's heartrate at wake time each day averages about 60 beats per minute (BPM) with a standard deviation of 3.5 BPM, a value of 90 BPM at wake time on a given day would represent a statistical outlier that may be indicative of an issue. In this case a medical professional could define a parameter that would be met based on occurrence of such a statistical outlier. The parameter could be specified in any desired manner. Using the specific example above, the parameter may be expressed as a number of standard deviations, for instance 3, from the average. This expresses a dynamic threshold, specifically lower and upper thresholds that define the ranges of outliers. A detected value below the lower threshold (3 standard deviations below average) or above the upper threshold (3 standard deviations above average) is considered an outlier that satisfies that dynamic parameter. The parameter is dynamic in that in this example it is dependent on the current window of values factoring into the determined average at the current time. Accordingly, a parameter need not be a hard threshold that necessarily is defined and met statically; it could instead be defined in a more abstract way.

Parameters are analyzed on the fly to recognize whether and when some criteria have been met based on the trigger event definitions, for instance doctor's settings, defining when to capture supplemental sensor data. As noted above, it may be burdensome or impossible to log all potentially relevant data at all times. In accordance with aspects described herein, primary data—such as data used in determining satisfaction of parameters for trigger conditions—may be captured (and optionally logged) and monitored to determine whether trigger condition(s) are met for triggering capture of supplemental sensor data. In this manner, supplemental data is obtained when deemed potentially important because it is reliant on a trigger condition being met. This avoids the resource cost of constantly capturing and logging this data.

Another configurable aspect may be the ability to set a number of interrupts or events that may be performed within a given period of time. The interrupts/events may include the prompting of the user to supply qualia input. It may be useful to set a cap on the number of interruptions in this regard pushed to the user, for instance in cases where a relevant event is sustained for a relatively long duration of time causing recognition of multiple triggers. The repeated triggers may be considered a common event requiring no relevant additional user input, though in some examples user qualia input taken across an event may be useful.

Some aspects relate to correlation of captured sensor data and qualia/sensation logging to create more complete records of health-related events. In this regard, three example scenarios are presented:

User-initiated qualia input before data trigger—It is possible that a doctor or other medical professional has not yet assigned specific parameters that are related to a condition that the patient has attempted to describe. Consequently, the trigger conditions may not yet be known. For these instances, the user may be able to trigger supplemental data capture by supplying self-perceived health status input. The user-initiated trigger is an example recognized health event. When the user experiences what the user perceives to be a potential health related issue, such as one the user previously experienced but was unable to convey in detail to the doctor, the user can provide the qualia input and trigger supplemental data capture for logging along with the qualia input and optionally primary sensor data to provide a more complete data record for the doctor. This may inform the doctor about the set of relevant parameters involved. The doctor can then use this information to define trigger conditions to trigger supplemental data capture going forward, i.e. without requiring the user to initiate qualia input for the system to recognize the event. The doctor may use this gathered information also to assist in diagnosing or perhaps refining existing trigger conditions to trigger supplemental sensor data capture.

In a data mining sense, user-initiated qualia input may an indication that the collection of signals (sensor data) at that point in time is important or relevant. An otherwise isolated look at the sensor data at that point in time, in the absence of the qualia indicating its importance, may not reveal any significance to the data. In some embodiments, the user-initiated qualia input sets up a set of statistical standards to further refine what exactly an 'outlier' may be.

User-initiated qualia input and simultaneous data trigger—In this situation, the device has detected a trigger condition based on monitoring primary sensor data and at substantially the same time the user has detected the condition. This can signify a strong correlation between the two, meaning the user's qualia input is likely directed at the recognized trigger condition.

Data trigger before user qualia input—This situation can occur when, based on monitoring primary sensor data, it is determined that one or more trigger conditions is met. This is another example of a recognized health event. The user can then be prompted to input the user's self-perceived health status. Additionally, supplemental sensor data capture and logging is initiated to provide the more complete sensor data record. In some examples, the wearable sensor device(s) are configured (powered, initiated, started, triggered, etc.) to obtain the supplemental sensor data. These wearable sensor device(s) may include the same or different sensor(s) than those capturing the primary sensor data and therefore may sense other information than that of the primary sensor data.

In addition to the above, on-line machine learning is possible through the user tagging of health events, in order to increase the sensitivity of heuristics/sensitivity-specificity of filters on the continuous biometric data streams from the sensor devices.

Figure 2:
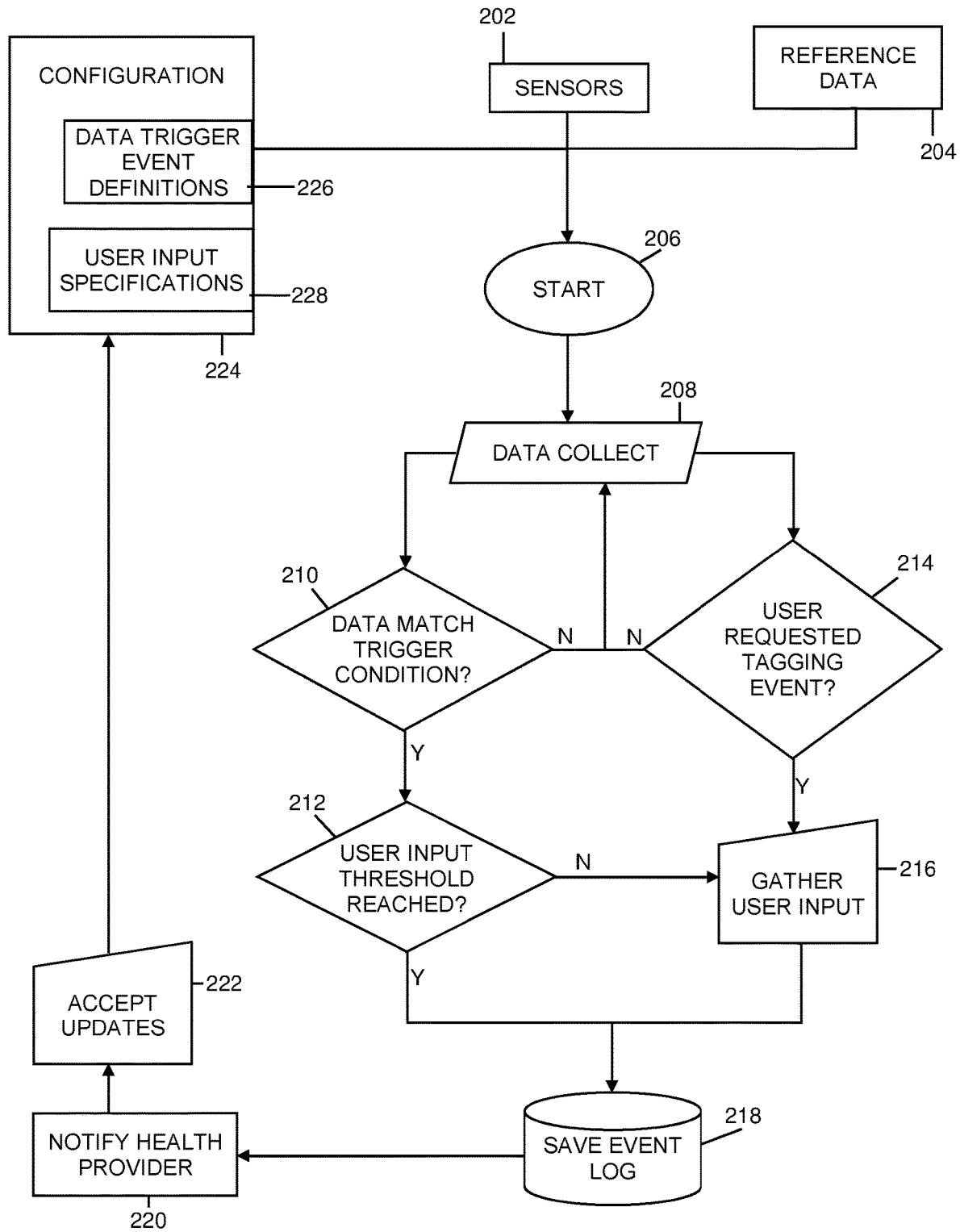
FIG. 2 depicts an example overview of triggered sensor data capture in a mobile device environment, in accordance with aspects described herein.

FIG. 2 depicts an example overview of triggered sensor data capture in a mobile device environment, in accordance with aspects described herein. Sensors 202, such as dedicated sensor device(s), wearable device(s), and/or other mobile device(s), supply sensor data into a process. The process may also accept or use reference data 204, which may be used in the checking of parameters of the trigger conditions to determine whether the parameters are met. Patient medical history, environmental factors, generally-accepted medical knowledge, weather forecasts, and air quality as just examples of some reference data that may be used. By way of specific example, reference data regarding local pollen count may be used to determine whether a parameter of 'pollen count=high' is met.

The process starting at 206 collects data (208) from the sensors and optionally reference data 204. Some sensor data may be primary sensor data obtained from one or more wearable sensor devices. The primary sensor data may be monitored to determine whether trigger condition(s) are met for triggering supplemental data capture.

The recognition of a health event is made in one example based on a determination (210) about whether a trigger condition of the trigger condition(s) has been met (e.g. the primary sensor data matches a trigger condition). As noted, a trigger condition may be a specified set of parameters and/or an indication based on statistical analysis of primary sensor data that supplemental logging may be useful. If it is determined at 210 that the primary sensor data does not match a trigger condition (210, N), then the process returns to data collection (208). Otherwise, if a health event was recognized in that it was determined that a trigger condition has been met (210, Y), it is then determined whether a user input threshold has been reached (212). It may be undesired to overburden a user with frequent prompts to supply self-perceived health status input. A threshold, in terms of frequency or other parameter, may be set by the user or another individual so that the solicitation of additional user input may be bypassed (described further below) in these cases.

Assuming the input threshold has not been reached (212, N), the process proceeds to gather user qualia in the form of self-perceived health status input (216). The solicitation for such input may be made in any desirable manner. The user may type or enter the input into an interface. This input may be guided, in the form of responses to specific questions that have been predefined and presented to the user for answering. Often times a doctor will want to ask questions particularized to the symptoms or detectable data experienced by the patient, so the user qualia may be supplied in response to these questions predefined by the doctor as part of the user input specifications 228 (described further below). In some cases, the input is a freeform narrative by the user. In addition, wearable sensor device(s), which may be the same or different devices from which the primary sensor data was obtained, are configured to obtain supplemental sensor data, which is in addition to the primary sensor data.

By way of specific example, a trigger condition may be detection of an elevated specific biometric parameter as observed from primary sensor data, together with an indication that the user ate food within the past 60 minutes. Upon determining that the data (e.g. elevated biometric parameter as sensed by a wearable sensor device) matches the trigger condition, the process determines whether the user input threshold has been reached (212). Assuming a trigger condition has not recently been met, the process can gather the user qualia input (216). Meanwhile, supplemental sensor data capturing may be initiated to log supplemental sensor data to provide a more detailed or granular log of relevant data, which might include data for other biometric parameters of the user, as an example. The supplemental sensor data capture may be configured to continue for a period of time, say 20 minutes, or until one or more parameters reach or revert back to a 'normal' state for instance. If within that period of time the same or another trigger condition is triggered, solicitation of additional user input may not be necessary or desired, and in fact may be considered intrusive to the user. In that case (212, Y), the process can bypass the solicitation for additional user input (216) and instead proceed directly from 212 to saving the qualia input, supplemental sensor data, and optionally primary sensor data to the event log (218).

Returning to 208 (data collection), the recognition of a health event is made in another example based on a determination about whether the user has requested tagging an event (214). In this situation, the user makes this request by initiating the input of qualia, or self-perceived health status information. Although the user may initiate this for any reason, a typical case will be when the user perceives a health issue or relevant condition about which information may be useful to the user's doctor or other medical professional. The system recognizes a health event, in this case the user's provision of the self-perceived health status input. As before, the system obtains this input (216) and configures wearable sensor device(s) to obtain the supplemental sensor data. Both sets of data are saved to the event log (218).

The obtained self-perceived health status input, supplemental sensor data, and optionally primary sensor data, may be correlated as health event data of a health event saved to the event log. This health event data may be provided for analysis, for instance by a health provider. The process therefore continues with notifying the health provider (220) about the correlated health event data. This data can be automatically pushed to a provider system, or pulled by the provider system from the system event log 218. Additionally or alternatively, the data may be transferred instantaneously or batch-transferred on a schedule, as examples. In particular example embodiments, the user's wearable device and/or mobile device performs the data collection and subsequent processing (210-218) including saving the correlated health event data to a local or remote storage, from which it is uploaded to, or downloaded by, a health provider computer system. There may optionally be an identification of types of health events that are considered more urgent than others in terms notifying the provider. Thus, some health event data may be provided in real-time or near real time as it is correlated, while other less urgent health event data may be provided according to a set schedule.

The process continues with the acceptance of the provided health event data as updates (222) to be analyzed. This can represent the point at which the doctor, other medical professional, or analytics system, as examples, has an opportunity to accept the data and optionally take any appropriate actions, such as making diagnoses, treatment plans, and/or changes to the configuration 224 in terms of what the trigger conditions 226 should be and the specification 228 of the user input prompts. The analysis of the updated health event data may inform whether modifications to the configuration should take place. The data trigger event definitions 226 are trigger conditions—sets of parameters being used for determining whether there is a data match to any trigger conditions (210). The user input specifications 228 may include information regarding the types of questions and specific questions to ask the user upon recognizing a health event. The health profession may determine to tune at least one trigger condition, to adjust a scope of supplemental sensor data capture. That is, by tuning the trigger condition, for instance adding, deleting, or modifying a parameter of the trigger condition, this changes how the trigger condition is satisfied and therefore the scope (timing, breadth, etc.) of supplemental sensor data capture.

The process then cycles back to 206 to provide continuous monitoring. As noted above, supplemental sensor data capture is deactivated (e.g. to save resources) at some point, depending on the configuration, event recognized, and/or any desired factors.

FIG. 2 shows the flexibility of managing the device(s) coordinating the correlated health event data capturing and ensuring that the most critical data is obtained and managed for the benefit of the patient. A feature provided is the partnership between the doctor, the patient, and the wearable devices involved. The doctor and patient can work together to focus on targeting the likely or suspected contributors to health events reported by the patient. The doctor can then configure the device to monitor a set of sensors and sets of triggers based on parameters and collected primary sensor data, and the patient responds to notifications from the device to annotate device-detected events. Alternatively, the patient can manually trigger logging based upon events the patient has experienced.

A device coordinating the correlated health event data capturing is in some examples a wearable sensor device like a smart watch or activity tracker/monitor. These wearable sensor devices typically include the sensor(s) providing the detected data values, though as illustrated in FIG. 1, they may be in communication with separate sensors providing sensor data. Alternatively, the coordinating device may be another mobile device such as a smartphone or tablet in communication with wearable device(s) and/or sensor(s). The coordinating device may serve as a hub to log data from multiple different sensors. The coordinating device can also be the device configured with the trigger condition(s) and performing the monitoring of the parameters of the trigger conditions to determine whether to trigger supplemental sensor data capture. In some embodiments a more hierarchical approach is taken for the data processing, where, for instance the triggering occurs at the sensor device level to perform the supplemental sensor data collection, while a more capable computer system like the user's smartphone may perform further processing, sorting, storing, and pushing health event data updates to the provider systems, as well as the configuration of the sensor devices with the trigger conditions.

The following example use cases or scenarios are provided to highlight some features described herein.

An elderly individual proceeding through a daily routine encounters a health issue that is life-threatening. The individual might not recognize the severity of the symptoms the individual experiences nor have the capacity to later remember and/or articulate to the medical professional what the user was feeling at the time the user realized the symptoms. If such a scenario were to exist, triggered sensor data capture described herein could provide better insights to the medical professionals or other authorities to administer care for the patient. One or more user devices may be configured to detect that something is wrong and then immediately solicit information from the user and commence supplemental sensor data capture in an attempt to capture any possibly relevant information about the issue. This logging may be especially useful for patients with memory disabilities.

Newborns, infants, and other pediatrics may have trouble communicating and conveying their symptoms. This can create major obstacles for the medical professionals when attempting to diagnose these types of patients. In some cases, the individual may be completely unable to communicate. Facilities provided herein could breakdown these barriers of communication and attempt to eliminate information uncertainty. This would provide the medical professional more accurate information upon which to base diagnoses. In some examples, a parent or caretaker of such an individual is prompted for qualia or other information about the individual.

An average middle-aged individual who is healthy and active might be under the impression there are minimal issues surrounding the individual's health. However, facilities provided herein are receptive to any irregular health issues and sudden changes, observed over a period of time such as several days, which if not addressed and left undetected can potentially cause detrimental damage to the individual's health. The health issue may be something that the individual does not currently notice. The proactive approach described herein instead of a reactive approach may be used to better understand when something otherwise undetected is important, and trigger robust data capture about the event. Additionally or alternatively, analytics platforms may be able to observe patterns and detect conditions that are otherwise undetectable and missed by individuals, even doctors or other trained experts. One example is the first onset of diabetes, which can be an unpredictable and potentially dangerous health-related event. Conditions may not manifest themselves in a human-observable form until there is a major issue with the individual's blood. Aspects described herein can monitor sensor data and identify before this onset of diabetes when there is or may be something wrong for which the individual should seek diagnosis.

Body-builders, runners, and other athletes continually strive to take their abilities to the next level, and each step presents an even greater risk toward harming the individual's overall health. Aspects described herein can properly detect and document sudden changes. This can enable the athlete to train harder, better, faster, and stronger while providing a means to monitor user health conditions and raise a flag if something problematic is indicated. Usually an athlete has a higher heartrate that normal. The medical professional can set thresholds and other parameters that are consistent with the reality that an athlete's parameters maybe very different from those of a less athletic individual.

Figure 3:
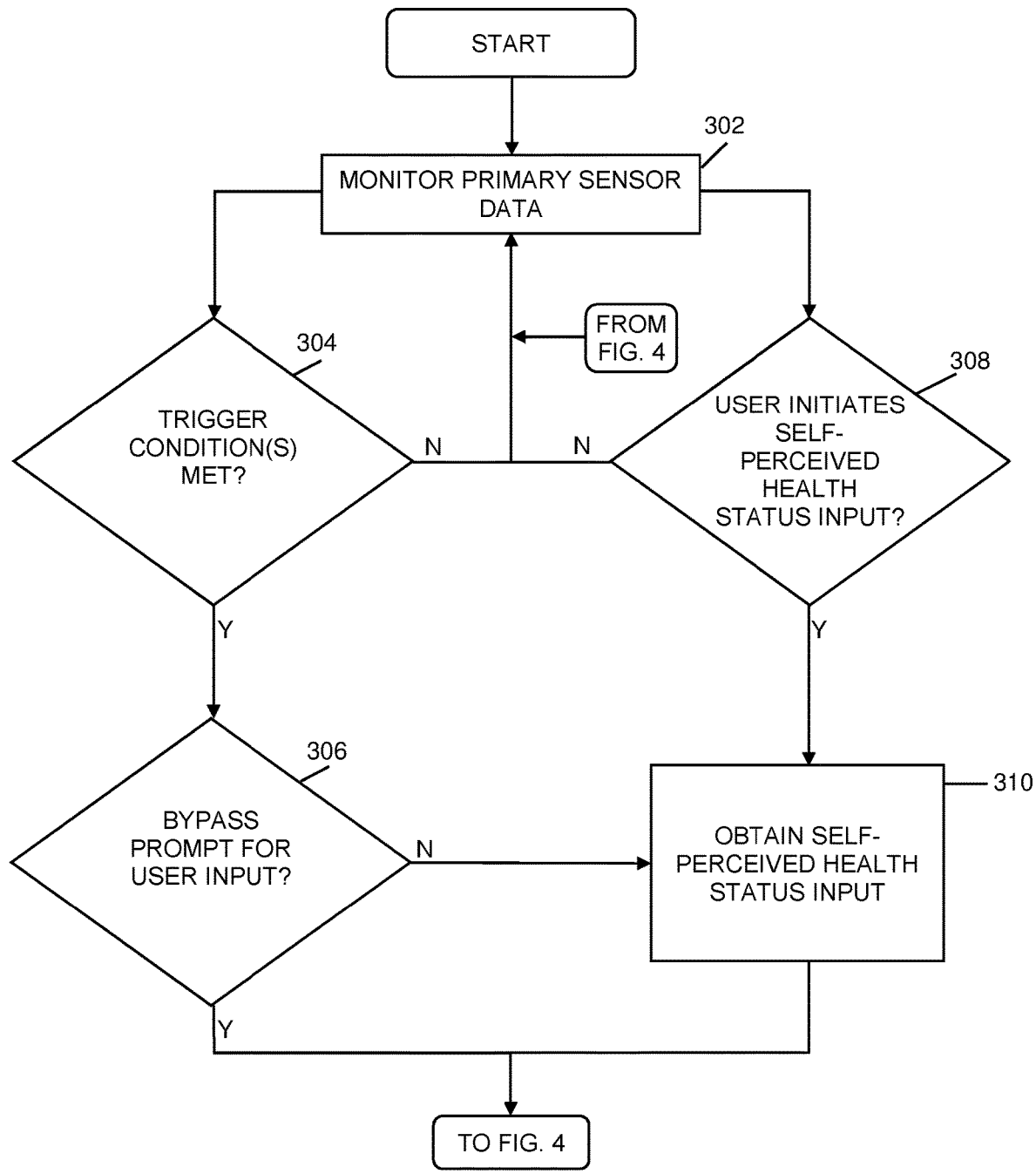
FIGS. 3 and 4 collectively depict an example process for triggered sensor data capture in a mobile device environment, in accordance with aspects described herein.
Figure 4:
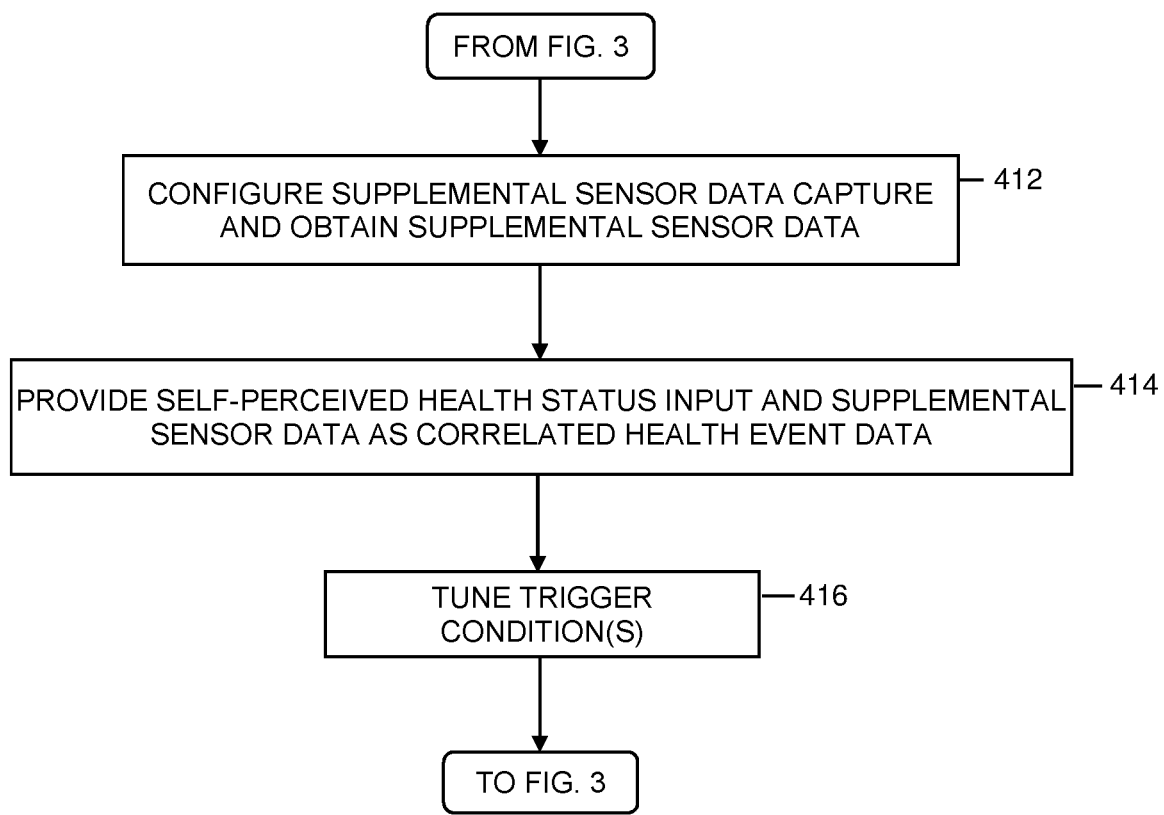

FIGS. 3 and 4 collectively depict an example of a process for triggered sensor data capture in a mobile device environment, in accordance with aspects described herein. In some examples, the process is performed one or more computer systems, such as those described herein, which may include one or more cloud servers, one or more wearable sensor devices, and/or one of more other devices.

Referring to FIG. 3, the process begins by monitoring primary sensor data (302). The primary sensor data may be obtained from at least one first wearable sensor device of one or more wearable sensor devices. In some examples, a wearable sensor device or other computer system in communication therewith performs this monitoring. The monitoring is used to determine whether one or more trigger conditions are met for triggering supplemental sensor data capture. The primary sensor data may be obtained with any frequency or schedule desired, such as on-demand or at a specific interval. Consequently, the primary sensor data values may change over time. The monitoring can be performed continually or at a set interval, for instance soon after each update of the primary sensor data values.

The process proceeds depending on whether a health event is recognized. In one aspect, it is determined whether trigger condition(s) have been met (304), and the health event is a recognition that a trigger condition of the one or more trigger conditions has been met. In some examples, a trigger condition includes one or more parameters, and the trigger condition is met based on the one or more parameters being satisfied, for instance primary sensor data and/or other data (weather conditions, time of day, etc.) indicating a particular condition or data value. A parameter of a trigger condition can include a dynamic threshold that is set dynamically, for instance based on statistical analysis of values of the primary sensor data. The occurrence of a statistical outlier in the values of primary sensor data is recognized when one or more values meets or exceeds (e.g. lower than a minimum threshold, higher than a maximum threshold) the dynamic threshold, thereby satisfying the parameter. In some examples, determining whether the trigger condition has been met uses reference data that can include any combination of one or more of the following: medical history of the user, environmental factors, and a body of generally-accepted medical knowledge.

If at 304 it is determined that no trigger condition has been met (304, N), the process continues back to 302 to further monitor primary sensor data. Otherwise, it is determined at 304 that a trigger condition has been met (304, Y) and the process continues by determining whether to bypass prompting the user for self-perceived health status input (306). This determination of whether to obtain self-perceived health status input from the user may be made based on occurrence of other health events. In some examples, the health event is a subsequent health event (second event) that occurs after a prior health event (first event). The process might recognize each health event based on one or more same or different trigger condition(s) of the one or more trigger conditions having been met. A determination may be made as to whether the subsequent health event was recognized within a threshold amount of time after the recognizing the prior health event. If so, both health events may be treated as related, perhaps indicating a common health issue or condition. The two events may be correlated as a single health event. In these cases, it may be desired to refrain from prompting the user for additional self-perceived health status input, especially if this was already obtained from the user after the prior event was recognized. In some examples, the prior-obtained self-perceived health status input is associated with the single health event absent obtaining additional self-perceived health status input from the user. Optionally, the prompt for this additional user input may be queued and delivered to the user after the threshold amount of time has lapsed, though in some examples no such prompt is made to the user after the recognized subsequent health event.

Assuming at 306 is it determined not to bypass the prompt for user input (306, N), the process proceeds by obtaining the self-perceived health status input (310). This may be obtained in response to prompting the user. The prompt may be in any desired form, for instance at least one question that solicits the self-perceived health status input from the user. Some or all of the at least one question may be selected based at least in part on the particular trigger condition that was met. In this regard, trigger conditions may be correlated to different questions, the answers to which may relate to the specific trigger condition that was met and/or the intent behind the defining and monitoring of the trigger condition. In this manner, medical professionals can solicit targeted user qualia input via questions specific to the trigger condition that prompts the qualia input.

Referring back to 302, in another aspect, a health event may be recognized based on determining whether the user initiates self-perceived health status input (308). If no such initiation is made (308, N), the process returns to 302. Otherwise, the health event is recognized if the user provides the self-perceived health status input (308, Y). The user can initiate provision of such input, and the user's initiation and provision of unprompted qualia input may be regarded as an indication of a potential health issue or condition that may not otherwise be recognized by a trigger condition or a review of sensor data being obtained at the time. The process continues by obtaining the self-perceived health status input (310), as explained above.

Whether proceeding directly from the inquiry at 306 (306, Y) or after obtaining self-perceived health status input (310), the process proceeds to FIG. 4. This triggers configuring at least one second wearable sensor device of the one or more wearable sensor devices to obtain supplemental sensor data. The supplemental sensor data includes additional data in addition to the primary sensor data. The first and second wearable sensor devices may be different sensor devices or may include one or more of the same sensor devices. The supplemental data may include data from other/additional sensors that sense and convey different information than what is conveyed in the primary sensor data. In some examples, the configuring of the second wearable sensor device(s) includes issuing commands to the device(s) to obtain the supplemental data, where the data was not currently already being obtained. This may include powering-on, waking, initiating, programming, etc. one or more of the second wearable sensor device(s) so that the supplemental data is being obtained and logged, either by them or by one or more remote devices. In some embodiments, the supplemental sensor data is already being captured by the second wearable sensor device(s) but is not being saved or logged, in which case the configuring configures the saving/logging of such supplemental sensor data.

In any event, the process continues by configuring the second wearable sensor device(s) for the supplemental sensor data capture and obtaining (saves, logs, etc.) that supplemental sensor data (412). The process then correlates the self-perceived user health status input and obtained supplemental sensor data together and, either in real-time or at a later time, provides the self-perceived health status input and the obtained supplemental sensor data as correlated health event data of the recognized health event (414). The correlated health event data may be provided to, as examples, a health provider, doctor, or other medical professional (e.g. computer systems thereof) for analysis. The process may also determine a schedule for this provision of the self-perceived health status input and the obtained supplemental sensor data, for example the schedule may be based at least in part on an urgency associated with the recognized health event. Health events for a condition recognized as being urgent or potentially urgent, such as a heart attack or diabetic shock, may warrant immediate provision of the related health event data.

An analysis of the provided correlated health event data may inform tuning of trigger condition(s) of the one or more trigger conditions (416), for instance to adjust a scope of supplemental sensor data capture. The tuning would adjust what triggers the capture of additional supplemental sensor data once that tuning is implemented. Tuning can refer to the configuration adjustments made by a health provider or other medical professional, the implementation of those adjustments on the involved wearable sensor device(s) or other mobile devices, or a combination of the two. This tuning can include definition of new trigger conditions and associated parameters, removal of existing trigger condition(s), and/or tweaking of existing trigger conditions, for instance modification (addition, deletion, change) to parameters of existing trigger condition(s).

In addition to the tuning of trigger condition(s), the analysis could further inform creation or modification of a set of questions to solicit health status input from the user based on a trigger condition of the one or more trigger conditions being met. The analysis could, for example, inform new question(s) to ask the user upon future triggers of one or more trigger conditions. As above, the creation/modification can refer to the adjustments made by a health provider or other medical professional, the implementation of those adjustments on the involved wearable sensor device(s) or other mobile devices, or a combination of the two.

Described herein are facilities for triggered sensor data capture in a mobile device environment, such as one including wearable devices having or using sensors to sense various biometric data of a user. Primary sensor data can be monitored to trigger solicitation of self-perceived health status input from a user by, e.g., asking data-driven questions, specifically in relation to qualia that may not otherwise be easily measured by sensors.

Additionally, trigger conditions can be tuned based on user input and/or event tagging, that is the correlation between self-perceived health status input and supplemental sensor data to provide correlated health event data. For instance, artificial intelligence adaptiveness can fine-tune the trigger conditions as a reactive process based on the sensor data that is being collected over time. The doctor or other medical professional can modify the parameters of the trigger conditions based on what the doctor sees in correlated health event data of the patient. Initially a specific "dragnet" of biometric screens (in the form of trigger conditions) may be created from a priori medical knowledge. The screens can then be fine-tuned through parameter adjustment and/or other adjustment, or addition to the trigger condition(s) to focus on what exactly is happening with the subject patient. Thus, capabilities of artificial intelligence may be leveraged in the analysis of the correlated health event data to accurately determine the condition that a user is experiencing. Captured sensor data alone may not be sufficient; the understanding of that data based on the correlation of detailed sensor data—the product of a targeted data gathering based on a recognized health event—with self-perceived user health status input provides useful information that an analytics platform, such as the Watson Analytics™ system offered by International Business Machines Corporation, Armonk, N.Y., USA (of which WATSON ANALYTICS is a trademark) can leverage to provide useful diagnoses, treatment, or other medical input.

Several improvements are realized. Capture of sensor data is synchronized with actual events detected, and supplemental sensor data supplements user self-perceived health status input. Instead of general background sensor monitoring, detailed and targeted data logging is provided, triggered by health events initiated by a user and/or determined based on checking parameters of various trigger conditions.

The captured sensor data may or may not be utilized immediately. In some approaches, wearable devices in particular communicate based on a timing scheme, rather than, in accordance with aspects described herein, being triggered by findings discovered in real time during, and based on, primary sensor data monitoring.

Journaling or scheduled sampling may not necessarily capture sensor data at a meaningful resolution that can be compared to events, and high-frequency journaling is burdensome and highly intrusive. Furthermore, smart watches and biometric wearables typically only log quantifiable items (heart rate, steps, temperature, etc.) without accounting for user qualia, or self-perceived health status. Mood journals have coarse data sampling and present difficulties correlating the data to specific, acute events.

Aspects described herein can provide selective data logging, and user-initiated triggers or potential disqualification of triggers (e.g. if the data suggests a health issue but the user qualia indicates otherwise) in a semi-supervised online and/or cloud-based learning format. In some aspects, instead of sensor feedback/metrics provided on discrete intervals, an opposite, trigger-based approach is provided. Data-mining, adaptive and/or machine-learning based associations may then be made between the triggers and captured sensor data. Additionally, this back-end can both learn and disqualify or modify trigger conditions where appropriate, especially when a large enough data set across various demographics is established.

Furthermore, the patient may provide unsolicited qualia input or the patient may be prompted for qualia input. Patient qualia input may be used to trigger logging of events in the form of correlated health event data for analysis.

Although various examples are provided, variations are possible without departing from a spirit of the claimed aspects.

Figure 5:
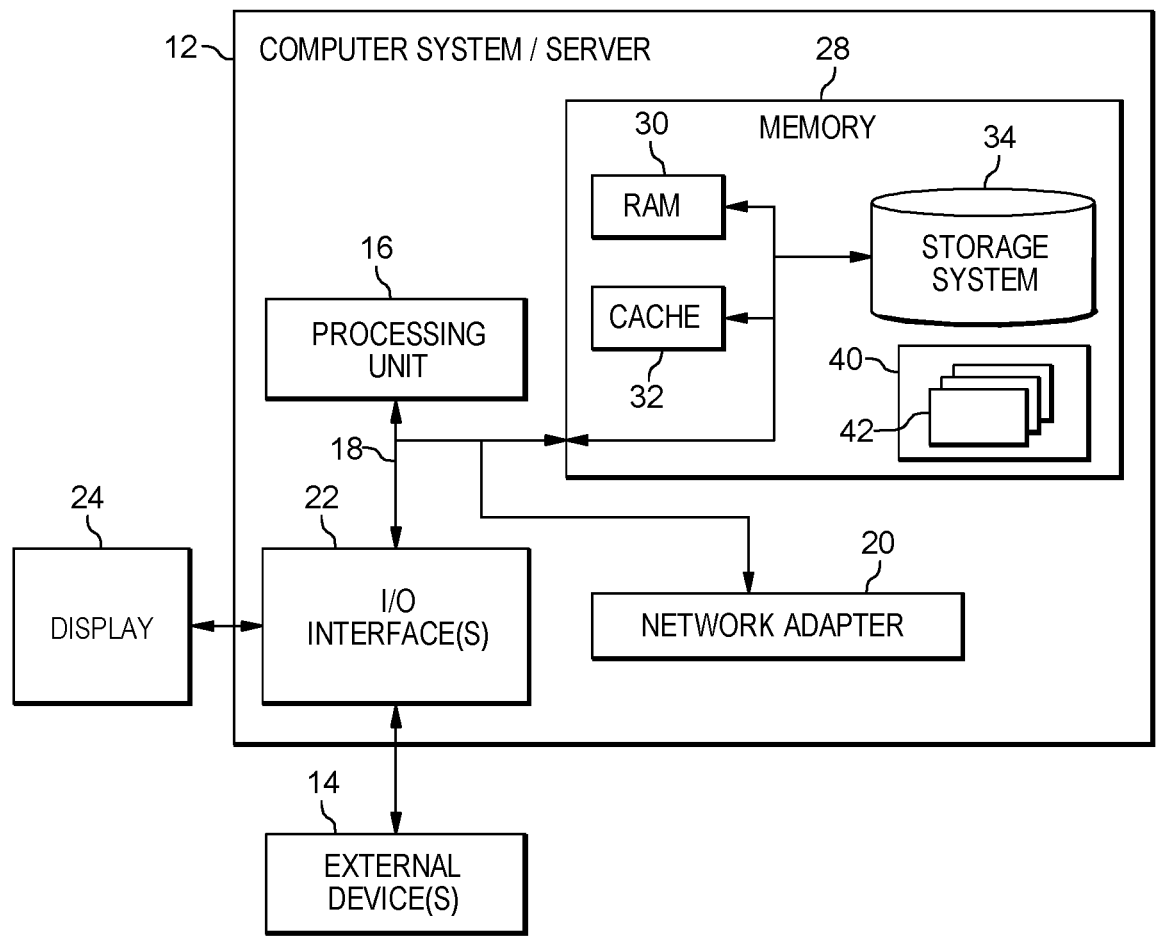
FIG. 5 depicts one example of a computer system and associated devices to incorporate and/or use aspects described herein.

Processes described herein may be performed singly or collectively by one or more computer systems, such as one or more wearable device or other mobile devices, one or more cloud servers or backend computers, or a combination of the foregoing. FIG. 5 depicts one example of such a computer system and associated devices to incorporate and/or use aspects described herein. A computer system may also be referred to herein as a data processing device/system or computing device/system/node, or simply a computer. The computer system may be based on one or more of various system architectures such as those offered by International Business Machines Corporation (Armonk, N.Y., USA), Intel Corporation (Santa Clara, Calif., USA), or ARM Holdings plc (Cambridge, England, United Kingdom), as examples.

As shown in FIG. 5, a computing environment 500 includes, for instance, a node 10 having, e.g., a computer system/server 12, which is operational with numerous other general purpose or special purpose computing system environments or configurations. Examples of well-known computing systems, environments, and/or configurations that may be suitable for use with computer system/server 12 include, but are not limited to, personal computer (PC) systems, server computer systems, thin clients, thick clients, workstations, laptops, handheld devices, mobile devices/computers such as smartphones, tablets, and wearable devices, multiprocessor systems, microprocessor-based systems, telephony device, network appliance (such as an edge appliance), virtualization device, storage controller set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in many computing environments, including but not limited to, distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media such as erasable programmable read-only memory (EPROM or Flash memory). By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments described herein.

Program/utility 40, having a set (at least one) of program modules 42, may be stored in memory 28 by way of example, and not limitation, as well as an operating system, one or more computer application programs, other program modules, and program data. Computer programs may execute to perform aspects described herein. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Input/Output (I/O) devices (including but not limited to microphones, speakers, accelerometers, gyroscopes, magnetometers, sensor devices configured to sense light, proximity, heart rate, body and/or ambient temperature, blood pressure, and/or skin resistance, activity monitors, GPS devices, cameras, etc.) may be coupled to the system either directly or through I/O interfaces 22. Still yet, computer system/server 12 may be able to communicate with one or more networks such as a local area network (LAN), a general wide area network (WAN), and/or a public network (e.g., the Internet) via network adapter 20. As depicted, network adapter 20 communicates with the other components of computer system/server 12 via bus 18. Network adapter(s) may also enable the computer system to become coupled to other computer systems, storage devices, or the like through intervening private or public networks. Ethernet-based (such as Wi-Fi) interfaces and Bluetooth® adapters are just examples of the currently available types of network adapters used in computer systems.

It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

One or more aspects may relate to cloud computing.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for loadbalancing between clouds).

A cloud computing environment is service oriented with a focus on statelessness, low coupling, modularity, and semantic interoperability. At the heart of cloud computing is an infrastructure comprising a network of interconnected nodes. One such node is node 10 depicted in FIG. 5.

Computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

Figure 6:
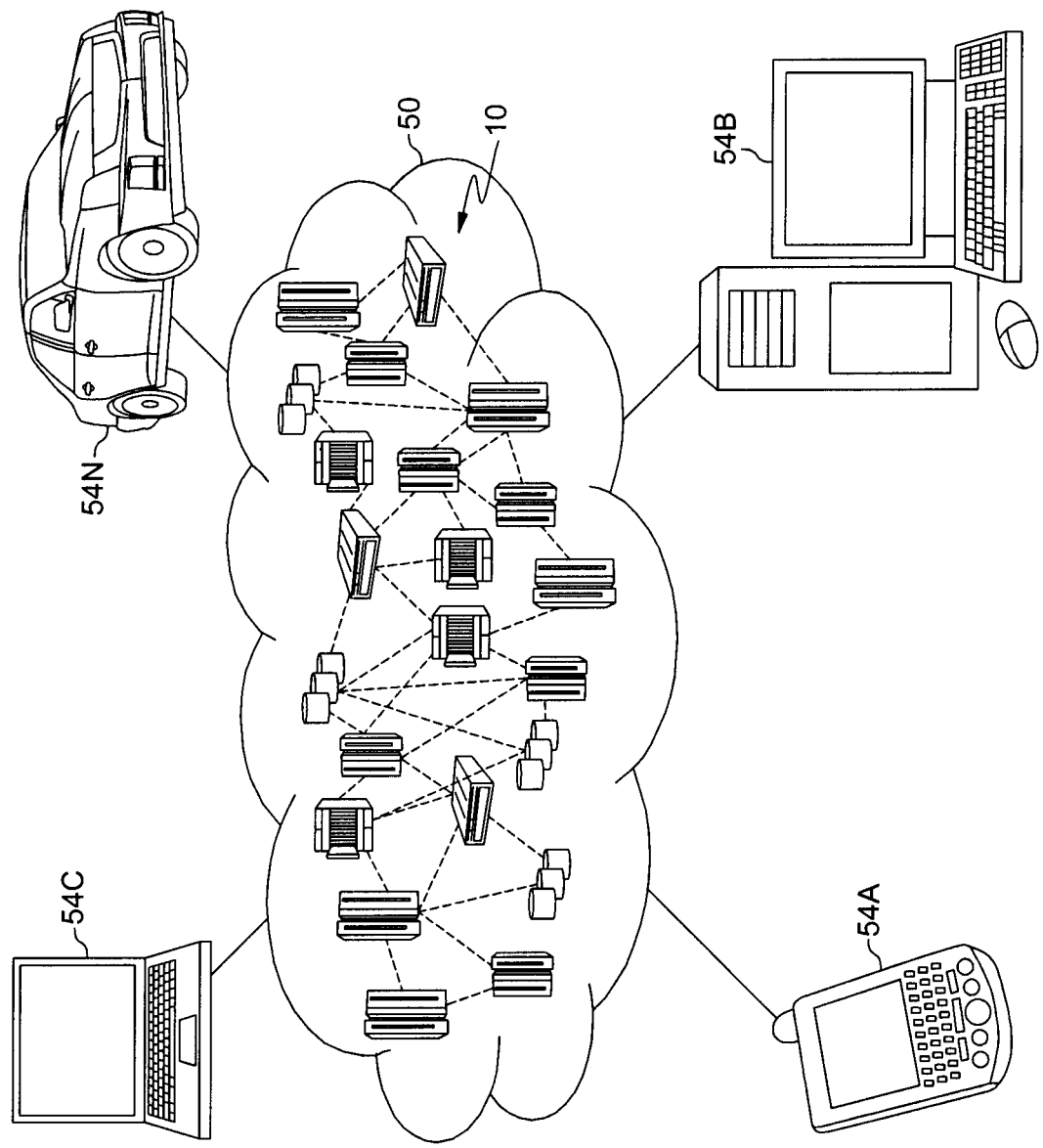
FIG. 6 depicts one embodiment of a cloud computing environment.

Referring now to FIG. 6, illustrative cloud computing environment 50 is depicted. As shown, cloud computing environment 50 comprises one or more computing nodes 10 with which local computing devices used by cloud consumers, such as, for example, smartphone or other mobile device 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
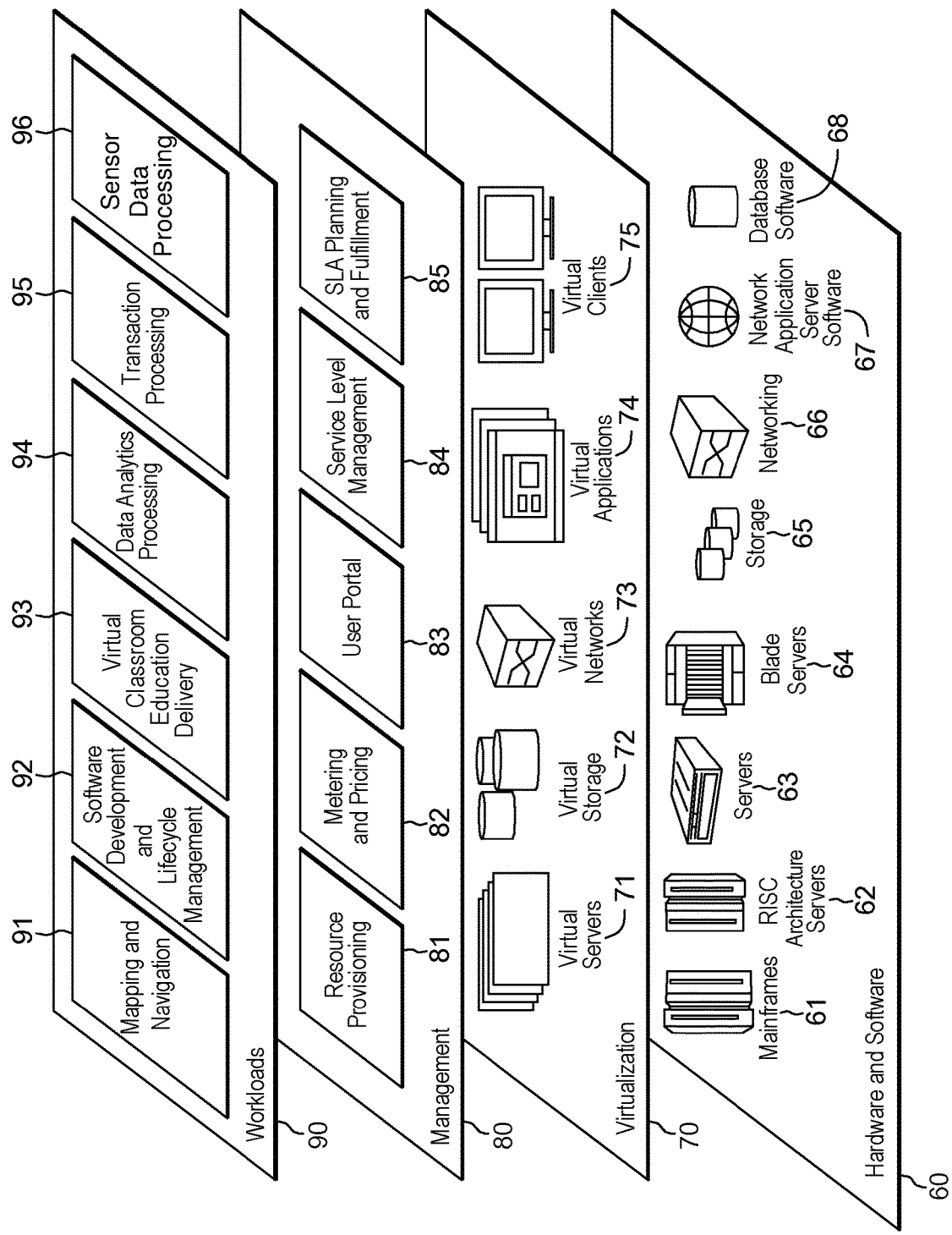
FIG. 7 depicts one example of abstraction model layers.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and sensor data processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, computing environments of other architectures can be used to incorporate and use one or more embodiments.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A method comprising:
monitoring primary sensor data obtained from at least one first wearable sensor device of one or more wearable sensor devices to determine whether one or more trigger conditions are met for triggering supplemental sensor data capture;
based on recognizing a first health event and on checking whether, and determining that, a threshold preventing obtaining self-perceived health status input from a user has not been satisfied, obtaining the self-perceived health status input from the user, configuring at least one second wearable sensor device of the one or more wearable sensor devices to obtain supplemental sensor data, the supplemental sensor data comprising additional data in addition to the primary sensor data, and obtaining the supplemental sensor data;
providing the self-perceived health status input and the obtained supplemental sensor data as correlated health event data of the first, health event for analysis;
based on the analysis of the correlated health event data, tuning at least one trigger condition of the one or more trigger conditions to adjust a scope of supplemental sensor data capture, wherein the one or more trigger conditions are defined and stored to a device, and wherein the tuning provides a changed trigger condition and stores a definition of the changed trigger condition to the device;
recognizing a second health event based on a trigger condition of the one or more trigger conditions being met; and
based on determining that the second health event is recognized within a threshold amount of time after the recognizing the first health event, correlating the first health event and the second health event as a single health event, wherein the obtained self-perceived health status input is associated with the single health event absent obtaining additional self-perceived health status input from the user until at least the threshold amount of time has lapsed.

2. The method of claim 1, wherein the first health event comprises the user providing the self-perceived health status input, wherein the providing the self-perceived health status input by the user triggers the configuring the at least one second wearable sensor device and the obtaining the supplemental sensor data.

3. The method of claim 1, wherein the recognizing the first, health event comprises determining that one of the trigger conditions of the one or more trigger conditions has been met, and wherein the method further comprises prompting the user to provide the self-perceived health status input in response to at least one question soliciting the self-perceived health status input from the user, the at least one question selected based at least in part on the one of the trigger conditions.

4. The method of claim 3, wherein the determining that the one of the trigger conditions has been met uses reference data comprising at least one selected from the group consisting of: medical history of the user, environmental factors, and a body of generally-accepted medical knowledge.

5. The method of claim 1, wherein one of the trigger conditions of the one or more trigger conditions comprises one or more parameters, wherein the one of the trigger conditions is met based on the one or more parameters being satisfied.

6. The method of claim 5, wherein a parameter of the one or more parameters comprises a dynamic threshold, the dynamic threshold set dynamically based on statistical analysis of values of the primary sensor data, such that occurrence of a statistical outlier in the values of primary sensor data exceeds the dynamic threshold and satisfies the parameter.

7. The method of claim 1, further comprising, based on the analysis of the correlated health event data, modifying an established set of questions for future presentation to the user to solicit health status input from the user based on one of the trigger conditions of the one or more trigger conditions being met, wherein the modifying is selected from the group consisting of: (i) adding one or more new questions to the established set of questions, and (ii) modifying an existing question of the established set of questions.

8. The method of claim 1, further comprising determining a schedule for the providing the self-perceived health status input and the obtained supplemental sensor data, the schedule based at least in part on an urgency associated with the recognized first health event.

9. The method of claim 1, wherein a scope of the supplemental sensor data capture is an initial scope for obtaining the supplemental sensor data, wherein the tuning the at least one trigger condition changes one or more parameters of a triggering condition that control whether the one or more trigger conditions are satisfied to trigger supplemental data capture, wherein the changing the one or more parameters adjusts the initial scope of supplemental sensor data capture to an adjusted scope of supplemental sensor data capture that is different from the initial scope of supplemental sensor data capture.

10. A computer program product comprising:
a computer readable storage medium readable by a processor and storing instructions for execution by the processor for performing a method comprising:
monitoring primary sensor data obtained from at least one first wearable sensor device of one or more wearable sensor devices to determine whether one or more trigger conditions are met for triggering supplemental sensor data capture;
based on recognizing a first health event and on checking whether, and determining that, a threshold preventing obtaining self-perceived health status input from a user has not been satisfied, obtaining the self-perceived health status input from the user, configuring at least one second wearable sensor device of the one or more wearable sensor devices to obtain supplemental sensor data, the supplemental sensor data comprising additional data in addition to the primary sensor data, and obtaining the supplemental sensor data;
providing the self-perceived health status input and the obtained supplemental sensor data as correlated health event data of the first health event for analysis;
based on the analysis of the correlated health event data, tuning at least one trigger condition of the one or more trigger conditions to adjust a scope of supplemental sensor data capture, wherein the one or more trigger conditions are defined and stored to a device, and wherein the tuning provides a changed trigger condition and stores a definition of the changed trigger condition to the device;
recognizing a second health event based on a trigger condition of the one or more trigger conditions being met; and
based on determining that the second health event is recognized within a threshold amount of time after the recognizing the first health event, correlating the first health event and the second health event as a single health event, wherein the obtained self-perceived health status input is associated with the single health event absent obtaining additional self-perceived health status input from the user until at least the threshold amount of time has lapsed.

11. The computer program product of claim 10, wherein the first health event comprises the user providing the self-perceived health status input, wherein the providing the self-perceived health status input by the user triggers the configuring the at least one second wearable sensor device and the obtaining the supplemental sensor data.

12. The computer program product of claim 10, wherein the first health event comprises determining that one of the trigger conditions of the one or more trigger conditions has been met, and wherein the method further comprises prompting the user to provide the self-perceived health status input in response to at least one question soliciting the self-perceived health status input from the user, the at least one question selected based at least in part on the one of trigger conditions.

13. The computer program product of claim 10, wherein one of the trigger conditions of the one or more trigger conditions comprises one or more parameters, wherein the one of the trigger conditions is met based on the one or more parameters being satisfied, and wherein a parameter of the one or more parameters comprises a dynamic threshold, the dynamic threshold set dynamically based on statistical analysis of values of the primary sensor data, such that occurrence of a statistical outlier in the values of primary sensor data exceeds the dynamic threshold and satisfies the parameter.

14. The computer program product of claim 10, wherein the method further comprises, based on the analysis of the correlated health event data, modifying an established set of questions to solicit health status input from the user based on one of the trigger conditions of the one or more trigger conditions being met, wherein the modifying is selected from the group consisting of: (i) adding one or more new questions to the established set of questions, and (ii) modifying an existing question of the established set of questions.

15. A computer system comprising:
a memory; and
a processing unit in communication with the memory, wherein the computer system is configured to perform a method, the method comprising:
monitoring primary sensor data obtained from at least one first wearable sensor device of one or more wearable sensor devices to determine whether one or more trigger conditions are met for triggering supplemental sensor data capture;
based on recognizing a first health event and on checking whether, and determining that, a threshold preventing obtaining self-perceived health status input from a user has not been satisfied, obtaining the self-perceived health status input from the user, configuring at least one second wearable sensor device of the one or more wearable sensor devices to obtain supplemental sensor data, the supplemental sensor data comprising additional data in addition to the primary sensor data, and obtaining the supplemental sensor data;

providing the self-perceived health status input and the obtained supplemental sensor data as correlated health event data of the first health event for analysis;

based on the analysis of the correlated health event data, tuning at least one trigger condition of the one or more trigger conditions to adjust a scope of supplemental sensor data capture, wherein the one or more trigger conditions are defined and stored to a device, and wherein the tuning provides a changed trigger condition and stores a definition of the changed trigger condition to the device;

recognizing a second health event based on a trigger condition of the one or more trigger conditions being met; and based on determining that the second health event is recognized within a threshold amount of time after the recognizing the first health event, correlating the first health even and the second health event as a single health event, wherein the obtained self-perceived health status input is associated with the single health event absent obtaining additional self-perceived health status input from the user until at least the threshold amount of time has lapsed.

16. The computer system of claim 15, wherein the first health event comprises the user providing the self-perceived health status input, wherein the providing the self-perceived health status input by the user triggers the configuring the at least one second wearable sensor device and the obtaining the supplemental sensor data.

17. The computer system of claim 15, wherein the first health event comprises determining that one of the trigger conditions of the one or more trigger conditions has been met, and wherein the method further comprises prompting the user to provide the self-perceived health status input in response to at least one question soliciting the self-perceived health status input from the user, the at least one question selected based at least in part on the one of the trigger conditions.

18. The computer system of claim 15, wherein one of the trigger conditions of the one or more trigger conditions comprises one or more parameters, wherein the one of the trigger conditions is met based on the one or more parameters being satisfied, and wherein a parameter of the one or more parameters comprises a dynamic threshold, the dynamic threshold set dynamically based on statistical analysis of values of the primary sensor data, such that occurrence of a statistical outlier in the values of primary sensor data exceeds the dynamic threshold and satisfies the parameter.

19. The computer system of claim 15, wherein the method further comprises, based on the analysis of the correlated health event data, modifying an existing set of questions to solicit health status input from the user based on one of the trigger conditions of the one or more trigger conditions being met, wherein the modifying is selected from the group consisting of: (i) adding one or more new questions to the established set of questions, and (ii) modifying an existing question of the established set of questions.

* * * * *